United States Patent [19]

Levine

[11] 4,213,979
[45] Jul. 22, 1980

[54] STABLE SPRAYABLE HYDROCORTISONE PRODUCT

[75] Inventor: Donald J. Levine, Memphis, Tenn.

[73] Assignee: Plough, Inc., Memphis, Tenn.

[21] Appl. No.: 970,705

[22] Filed: Dec. 18, 1978

[51] Int. Cl.$^2$ ............................................. A61K 31/56
[52] U.S. Cl. .................................................. 424/243
[58] Field of Search ..................... 424/243; 260/397.45

[56] References Cited

U.S. PATENT DOCUMENTS 4,083,974  4/1978  Turi ...................................... 424/243

Primary Examiner—Elbert L. Roberts
Attorney, Agent, or Firm—Vincent H. Gifford; Bruce M. Eisen

[57] ABSTRACT

A cosmetically elegant and stable topical anti-inflammatory and antipruritic hydrocortisone solution, stabilized for use in a non-aerosol spray assembly with PPG-12-PEG-50-Lanolin.

16 Claims, No Drawings

STABLE SPRAYABLE HYDROCORTISONE PRODUCT

BACKGROUND OF THE INVENTION

This invention relates to a stable, cosmetically elegant hydrocortisone hydroalcoholic solution useful for the relief of itching and inflammation associated with minor skin irritation when applied as a non-aerosol spray. It is relatively non-flammable and exhibits no microscopic crystallization. The preparation is primarily designed for the treatment of poison ivy and contact dermatitis, although it would also be useful for the treatment of minor burns, cuts, scratches, sunburn and other similar minor skin irritants.

Hydrocortisone, which is a naturally occuring steroid, is a white powder that is very slightly soluble in water but soluble in alcohol and glycol solvents. Its solubility at 25° C. in water, ethanol and propylene glycol is 0.28, 15.0 and 12.7 mg/ml, respectively. It is also known as cortisol.

Hydrocortisone has been marketed in the United States since 1952 as a prescription drug and is recognized as one of the most potent and effective agents for the treatment of many common dermatoses. It has been commonly used for many years in various topical prescription preparations as an antipruritic and anti-inflammatory agent in the 0.5-5.0 percent dosage range. In recent years it has been used topically in a dosage range of 0.1-0.25 percent. It has recently been recommended by the OTC Topical Analgestic Panel of the FDA as a safe and effective topical analgesic product when applied at 0.25-0.50 percent to affected areas of the skin 3 to 4 times daily.

Topical hydrocortisone compositions have traditionally been sold in the form of ointments, lotions and creams. In U.S. Pat. No. 3,456,052 an aerosol ointment form was disclosed. Hydroalcoholic lotion solutions are also known but are generally found to be unstable, particularly at low temperature, with small amounts of hydrocortisone crystallizing out. This problem is not a great concern in these preparations since a small degree of crystallization will usually not seriously affect the use of a lotion which is rubbed on the skin, although if the crystallization is severe enough it could irritate inflamed, sensitive skin. In a spray device this problem is serious since even microscopic crystals can block the outlet orifice of the container and render the device inoperable.

The spray is a particularly desirable form since it is convenient and presents no danger of contamination to the product. A spray would also provide a generally cooling effect on the inflamed skin and cause less irritation to sensitive skin than would be produced by the rubbing on of a lotion or the like. However, the aerosols containing fluorocarbon propellants are undesirable for environmental reasons and the hydrocarbon propellants are highly flammable.

DETAILED DESCRIPTION OF INVENTION

I have now surprisingly discovered a stable, relatively non-flammable, cosmetically elegant, sprayable topical hydrocortisone composition which is particularly suited for use in a non-aerosol spray assembly.

The key ingredient in the formulation which stabilizes the hydrocortisone is polyoxypropylene-(12)-polyoxyethylene-(50)-lanolin. This compound, whose CTFA recognized name is PPG-12-PEG-50-Lanolin, is the polyoxypropylene, polyoxyethylene derivative of lanolin that conforms generally to the formula

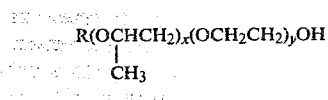

where R represents the lanolin radicals, x has an average value of 12 and y has an average value of 50. It is sold commercially under the tradename LANEXOL AWS by Croda, Inc. Its principal use has been in hair preparations, soaps, creams, antiperspirants and lotions where the properties of lanolin would be advantageous.

The preferred formulation particularly suited for use in a pump spray device is an aqueous solution containing 0.2-1.0 percent of hydrocortisone; 0.2-1.0 percent of polyoxypropylene-(12)-polyoxyethylene-(50)-lanolin; 15-35 percent of a cosmetically acceptable, water-miscible alcohol solvent in which the hydrocortisone is soluble; 10-35 percent of a cosmetically acceptable glycol solvent which is a liquid at 25° and in which the hydrocortisone is soluble; and at least 50 percent water. The resulting formulation is physically stable at low temperatures, chemically stable at higher temperatures, does not excessively dry the skin, exhibits a good spray pattern, and does not exhibit the high flammability characteristically associated with high concentrations of flammable solvents.

The most preferred pump spray formulations contain 0.25 to 0.5 percent of hydrocortisone and 0.3 to 0.7 percent of the polyoxypropylene-(12)-polyoxyethylene-(50)-lanolin. This formula would also preferably contain 15-25 percent of ethanol; 10-25 percent of propylene glycol, wherein the maximum concentration of the alcohol and glycol solvents is 45 percent; and 55-60 percent of water. Another suitable water-miscible alcohol solvent is isopropyl alcohol. Other suitable water-miscible glycol solvents are polypropylene glycol and peroxide-free polyethylene glycol having a molecular weight of 200-600.

The formulation can be utilized in conjunction with any non-aerosol spray assembly. Many such spray assemblies are widely known and used, such as the squeeze spray assembly shown in U.S. Pat. Nos. 3,361,304 and 3,474,936 (which are herein incorporated by reference), or the pump spray system shown in U.S. Pat. Nos. 4,010,874 and 4,022,354 (which are also herein incorporated by reference). The spray assembly will generally comprise a reservoir for holding the sprayable composition; a means for mixing the composition with air; and a means to dispense the air/liquid mixture as a spray. This is usually accomplished by creating a pressure differential between the atmosphere and the inside of the container, e.g. a pumper or squeezing a resilient container wall.

I have found that in our alcohol-glycol system the hydrocortisone is particularly stable at a pH of 4.0-5.0. In order to achieve this preferred pH range, it is generally necessary to downwardly adjust the pH of the formulation with a suitable dilute acid solution, e.g. 20% w/w phosphoric acid solution. It is generally known that hydrocortisone is more stable in an acid environment but it was not generally known that a narrow pH range of 4.0-5.0 was particularly suited in an alcohol-glycol aqueous system.

Various optional ingredients may be included in the formulation such as perfumes; preservatives, e.g. parabens; antiseptics, e.g. triclosan, phenol; humectants; emollients; antioxidants; chelating agents, e.g. disodium EDTA; dyes; foaming agents; as well as any other class of material whose presence may be cosmetically or otherwise desirable.

The following non-limiting Examples are presented to illustrate the invention. The terminology is in conformance to the CTFA Cosmetics Ingredient Dictionary, published by the Cosmetic, Toiletries and Frangrance Assoc., Wash., D.C., 2nd Edition, 1977. The percentages used throughout the specification are weight percents unless indicated otherwise.

EXAMPLE 1

A topical anti-inflammatory solution is prepared according to the following preferred formulation:

| Part A | |
| --- | --- |
| Hydrocortisone | 0.5 |
| Ethanol | 20.0 |
| Propylene Glycol | 20.0 |
| Part B | |
| PPG-12-PEG-50-Lanolin | 0.5 |
| Disodium EDTA | 0.1 |
| Water | 58.9 |
| | 100.0 |

The ingredients of Part A are agitated at room temperature until all solids dissolve. The ingredients of Part B are agitated at room temperature until all solids dissolve. The mixture of Part A is then blended with the mixture of Part B. The pH of the resulting formulation is downwardly adjusted from 6.4 to 4.5 with a dilute phosphoric acid solution.

EXAMPLE 2

| Part A | |
| --- | --- |
| Hydrocortisone | 0.5 |
| Alcohol | 30.0 |
| Propylene Glycol | 10.0 |
| Part B | |
| PPG-12-PEG-50-Lanolin | 0.5 |
| Disodium EDTA | 0.1 |
| Water | 58.9 |
| | 100.0 |

The above formula is prepared in a similar manner to Example 1. The pH of the resulting formulation is downwardly adjusted from 6.5 to 4.5 with a dilute phosphoric acid solution.

EXAMPLE 3

| Part A | |
| --- | --- |
| Hydrocortisone | 0.5 |
| Alcohol | 15.0 |
| Propylene Glycol | 25.0 |
| Part B | |
| PPG-12PEG-50-Lanolin | 0.5 |
| Methyl Paraben | 0.2 |
| Water | 58.8 |
| | 100.0 |

The above formula is prepared in a manner similar to Example 1. The pH of the resulting formulation is downwardly adjusted from 6.2 to 4.5 with a dilute hydrochloric acid solution.

EXAMPLE 4

| Part A | |
| --- | --- |
| Hydrocortisone | 0.5 |
| Alcohol | 15.0 |
| Propylene Glycol | 25.0 |
| Part B | |
| PPG-12-PEG-50-Lanolin | 1.0 |
| Methyl Paraben | 0.2 |
| Water | 58.3 |
| | 100.0 |

The above formula is prepared in a manner similar to Example 1. The pH of the resulting formulation is downwardly adjusted from 6.2 to 4.5 with a dilute citric acid solution.

Formulas prepared according to the above Examples provide a soothing and cooling effect when sprayed on inflamed skin. The formulations are physically stable at low temperatures, chemically stable at high temperatures, and do not block the orifice when used in a non-aerosol spray device. They provide a good spray pattern when sprayed from a pump dispenser. They do not unduly dry the skin and are relatively non-flammable.

Numerous other variants of the above formulations will be apparent to one skilled in the art and within the spirit of the invention.

What is claimed is:

1. An anti-inflammatory, antipruritic aqueous solution comprising hydrocortisone and PPG-12-PEG-50-Lanolin.

2. The composition of claim 1 wherein the concentration of hydrocortisone is 0.2 to 1.0 percent.

3. The composition of claim 2 wherein the concentration of hydrocortisone is 0.2 to 0.5 percent.

4. The composition of claim 3 wherein the concentration of hydrocortisone is 0.5 percent.

5. The composition of claim 3 wherein the concentration of said lanolin derivative is 0.2–1.0 percent.

6. The composition of claim 1 further comprising a water-miscible glycol solvent in which the hydrocortisone is soluble and wherein the alcohol is a water-miscible alcohol solvent in which the hydrocortisone is soluble.

7. The composition of claim 6 wherein the concentration of said alcohol solvent is 15–35 percent and the concentration of said glycol solvent is 10–35 percent.

8. The composition of claim 7 wherein the concentration of said alcohol solvent is 15–25 percent and the concentration of said glycol solvent is 10–25 percent, wherein the maximum concentration of said solvents is 45 percent.

9. The composition of claim 8 wherein said alcohol solvent is ethanol and said glycol solvent is propylene glycol.

10. The composition of claim 8 wherein the concentration of water is at least 50 percent.

11. The composition of claim 10 wherein the concentration of the water is 55–60 percent.

12. The composition of claim 1 wherein the pH of the formulation is 4.0–5.0.

13. The composition of claim 12 wherein the pH of the composition is 4.5.

14. A topical anti-inflammatory product comprising a non-aerosol spray assembly; and the composition of claim 1 within said assembly; wherein said assembly comprises a reservoir for holding said composition, a means for mixing the composition with air and a means to dispense the air/liquid mixture as a spray.

15. A method of alleviating inflammation and pruritis in the skin of a person suffering from a minor skin irritation comprising the step of spraying onto said inflamed skin an effective amount of the composition of claim 1.

16. The composition of claim 1 wherein said solution is a hydroalcoholic solution.

* * * * *